(12) United States Patent
Periaswamy et al.

(10) Patent No.: US 8,983,156 B2
(45) Date of Patent: Mar. 17, 2015

(54) SYSTEM AND METHOD FOR IMPROVING WORKFLOW EFFICIENCIES IN READING TOMOSYNTHESIS MEDICAL IMAGE DATA

(71) Applicant: iCAD, Inc., Nashua, NH (US)

(72) Inventors: Senthil Periaswamy, Hollis, NH (US); Sergey Fotin, Nashua, NH (US)

(73) Assignee: iCad, Inc., Nashua, NH (US)

( * ) Notice: Subject to any disclaimer, the term of this patent is extended or adjusted under 35 U.S.C. 154(b) by 73 days.

(21) Appl. No.: 13/684,475

(22) Filed: Nov. 23, 2012

(65) Prior Publication Data
US 2014/0147025 A1  May 29, 2014

(51) Int. Cl.
| G06K 9/00 | (2006.01) |
| G06T 7/00 | (2006.01) |
| A61B 6/02 | (2006.01) |
| A61B 6/00 | (2006.01) |

(52) U.S. Cl.
CPC .............. G06T 7/0012 (2013.01); A61B 6/025 (2013.01); A61B 6/502 (2013.01); A61B 6/5223 (2013.01); A61B 6/466 (2013.01); A61B 6/469 (2013.01)
USPC ............................ 382/128; 382/131; 382/100

(58) Field of Classification Search
None
See application file for complete search history.

(56) References Cited

U.S. PATENT DOCUMENTS

| 6,389,104 | B1 * | 5/2002 | Bani-Hashemi et al. | .. 378/98.12 |
| 7,346,381 | B2 * | 3/2008 | Okerlund et al. | ............. 600/407 |
| 7,630,533 | B2 | 12/2009 | Ruth et al. | |
| 8,044,972 | B2 | 10/2011 | Hall et al. | |
| 8,051,386 | B2 | 11/2011 | Rosander et al. | |
| 8,155,421 | B2 | 4/2012 | Ren et al. | |
| 2004/0008901 | A1 * | 1/2004 | Avinash | ......................... 382/260 |
| 2006/0018526 | A1 * | 1/2006 | Avinash | ......................... 382/132 |
| 2009/0005668 | A1 * | 1/2009 | West et al. | ..................... 600/407 |

FOREIGN PATENT DOCUMENTS

| EP | 2301432 A1 | 3/2011 |
| WO | 2011091300 A2 | 7/2011 |
| WO | 2012063653 A1 | 5/2012 |

* cited by examiner

*Primary Examiner* — Avinash J Yentrapati
(74) *Attorney, Agent, or Firm* — Loginov & Associates, PLLC; William A. Loginov

(57) ABSTRACT

A system and a method are disclosed that forms a novel, synthetic, two-dimensional image of an anatomical region such as a breast. Two-dimensional regions of interest (ROIs) such as masses are extracted from three-dimensional medical image data, such as digital tomosynthesis reconstructed volumes. Using image processing technologies, the ROIs are then blended with two-dimensional image information of the anatomical region to form the synthetic, two-dimensional image. This arrangement and resulting image desirably improves the workflow of a physician reading medical image data, as the synthetic, two-dimensional image provides detail previously only seen by interrogating the three-dimensional medical image data.

24 Claims, 4 Drawing Sheets

SYSTEM AND METHOD FOR IMPROVING WORKFLOW EFFICIENCES IN READING TOMOSYNTHESIS MEDICAL IMAGE DATA

BACKGROUND

1. Field of the Invention

This application relates generally to image processing for biomedical applications. More particularly, this application relates to improving workflow efficiencies in reading medical image data.

2. Description of the Related Art

In the fields of medical imaging and radiology, various techniques may be employed for creating images of an anatomical region of the human body. For example, in mammography, the breast is often imaged at two fixed angles using x-rays. Physicians may review two-dimensional (2D) or planar x-ray images of the anatomical region to uncover and diagnose disease-like conditions, such as breast cancer.

Numerous medical imaging procedures now employ systems and techniques that create three-dimensional (3D) or volumetric imagery of the human body. For example, significant attention has been given to tomographic imaging techniques. One such example is digital breast tomosynthesis (DBT), a relatively new imaging procedure in which systems image a breast by moving a source and exposing the breast to radiation from a plurality of angles, thus acquiring high resolution, planar images (i.e., "direct projections") at different angles. For example, a DBT system may acquire 10 direct projection images in which the source moves in such a way as to change the imaging angle by a total angle of 40 degrees.

3D medical images enable physicians to visualize important structures in greater detail than available with 2D medical images. However, the substantial amount of image data produced by 3D medical imaging procedures presents a challenge. In mammography, for example, a physician may review two images of a breast: a cranial-caudal (CC) image and a medial-lateral oblique (MLO) image. In DBT, the physician may review approximately 50-70 images, which could include the original projection images and reconstructed images.

Several techniques for improving the speed of diagnostic assessment are disclosed in U.S. Pat. No. 7,630,533, entitled BREAST TOMOSYNTHESIS WITH DISPLAY OF HIGHLIGHTED SUSPECTED CALCIFICATIONS; U.S. Pat. No. 8,044,972, entitled SYNCHRONIZED VIEWING OF TOMOSYNTHESIS AND/OR MAMMOGRAMS; U.S. Pat. No. 8,051,386, entitled CAD-BASED NAVIGATION OF VIEWS OF MEDICAL IMAGE DATA STACKS OR VOLUMES; and U.S. Pat. No. 8,155,421, entitled MATCHING GEOMETRY GENERATION AND DISPLAY OF MAMMOGRAMS AND TOMOSYNTHESIS IMAGES, the teachings of which patents are incorporated herein by reference as useful background information. However, solutions are desired that would further improve the speed of diagnosis without sacrificing the detail provided by 3D medical imaging technology.

SUMMARY OF THE INVENTION

This invention overcomes disadvantages of the prior art by providing a system and method for improving workflow efficiencies in reading tomosynthesis medical image data that avoids sacrificing desired detail in images. The system and method generally enhances the identification of regions and/or objects of interest (ROIs), such as masses, within an acquired image by performing, based on three-dimensional (3D) data, an enhancement process to the image before it is projected into a two-dimensional (2D) format. This renders the regions/object(s) of interest more identifiable to a viewer (e.g. a diagnostician, such as a physician and/or radiologist) in the 2D-projected image as it boundaries are more-defined within the overall field.

In an illustrative embodiment, the system and method acquires, using an acquisition process, one or more two-dimensional (2D) regions of interest (ROIs) from a three-dimensional (3D) medical image of an anatomical region. The medical image is obtained from a scanning process carried out on a patient by an appropriate medical imaging device and associated data handling and storage devices. A first projection process defines a first 2D projection image of the anatomical region. Then, a second projection process generates a second 2D projection image of the anatomical region using image information from the first 2D projection image and the one or more 2D ROIs. The second 2D projection image is then output to be stored and/or displayed using an appropriate storage system and/or display device. The second projection process can be constructed and arranged, in a blending process, to blend the one or more 2D ROIs with image information from the first 2D projection image, and can include an ROI detector that forms at least one ROI response image. The blending process can be further constructed and arranged to extract 2D binary masks of the one or more ROIs from at least one ROI response image and/or to blend the 2D binary masks with the first 2D projection image to generate the second 2D projection image. Additionally, a three-dimensional response image based upon a selected portion of the second 2D projection image can be provided to assist the diagnostician in identifying a region or object of interest, such as a mass. This 3D response image characterizes the degree to which various points or regions in an image exhibit characteristics interest.

BRIEF DESCRIPTION OF THE DRAWINGS

Various inventive embodiments disclosed herein, both as to its organization and manner of operation, together with further objectives and advantages, may be best understood by reference to the following description, taken in connection with the accompanying drawings as set forth below in which.

DETAILED DESCRIPTION

Figure 1:
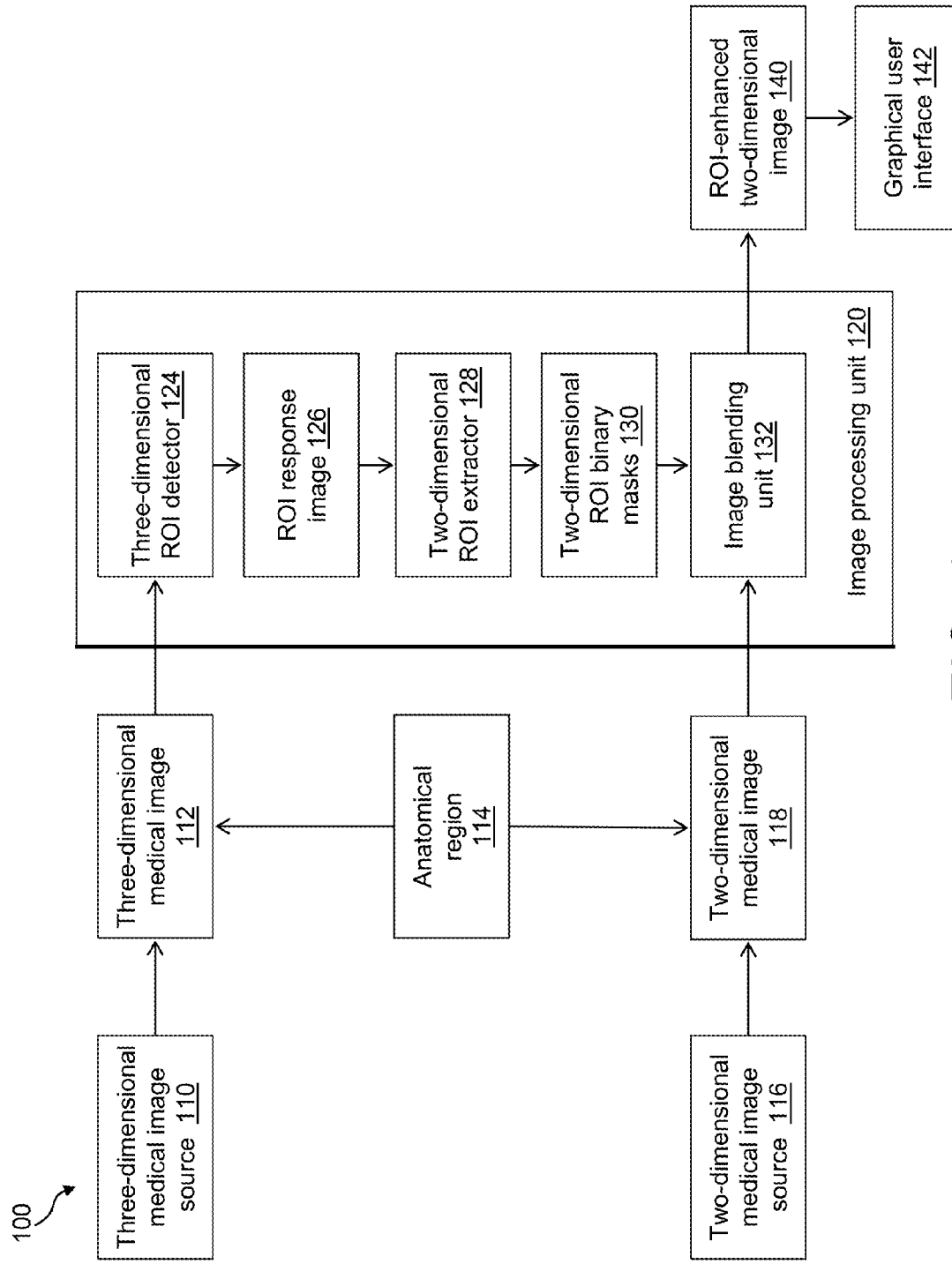
FIG. 1 is a block diagram of a medical imaging system according to an illustrative embodiment.

FIG. 1 is a block diagram of a medical imaging system 100 in accordance with an illustrative embodiment. The system includes a three-dimensional medical image source 110, a two-dimensional medical image source 116, and an image processing unit 120 that produces a novel, region of interest (ROI)-enhanced two-dimensional image 140 that can be the primary image read for detection and diagnosis of disease by a diagnostician. The system 100 further includes a graphical user interface (GUI) and/or display 142 for outputting the various medical image data. It should be noted that a wide range of functional components can be provided to the system, 100 in various embodiments, including various networked data-handling and storage devices, additional displays, printing devices, interfaces for portable computing devices, etc.

According to an embodiment, the three-dimensional medical image source 110 is a digital tomosynthesis imaging system such as offered by the General Electric Company of Fairfield, Conn. (GE); Hologic, Inc, of Bedford, Mass. (Hologic); or Siemens AG of Munich, Germany (Siemens). Digital tomosynthesis imaging systems image an anatomical region by moving a source, and acquiring a plurality of projection images (e.g., 10-25 direct projections) at different angles (e.g., at 4-degree increments).

As illustrated in FIG. 1, the three-dimensional medical image source 110 provides a three-dimensional image 112 of an anatomical region 114. According to an embodiment, after the source 110 acquires projection images, the projection images are input to a reconstruction processing unit, which employs conventional techniques and processes to construct an image volume of the anatomical region. By way of one example, the image volume can be constructed in 40-60 image thin slices, each thin slice having a spatial resolution of 100 microns per pixel, a thickness of 1 millimeter (mm), and dimensions of 2500 rows of pixels by 1500 columns of pixels.

According to an embodiment, the two-dimensional medical image source 116 provides a two-dimensional image 118 of the anatomical region 114. By way of one example, source 116 can include a computer memory of conventional design that reads the image 118 from a disk or other data storage device. The depicted source can be defined to include associated storage hardware in such embodiments. By way of another example, source 116 can be defined to include a tomosynthesis image acquisition unit capable of operating in a full-field digital mammography imaging mode and acquiring medio-lateral oblique (MLO) or cranio-caudal (CC) two-dimensional images. By way of yet a further example, source 116 can be defined to include image processing computer software capable of synthetically producing two-dimensional images from existing image data of the anatomical region 114.

Note, as used herein the terms "process" and/or "processor" should be taken broadly to include a variety of electronic hardware and/or software based functions and components. Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor here herein can be implemented using electronic hardware, software consisting of a non-transitory computer-readable medium of program instructions, or a combination of hardware and software.

The image processing unit 120 further includes a three-dimensional ROI detector 124, a two-dimensional ROI extractor 128, and an image blending unit 132.

The three-dimensional ROI detector 124 characterizes the degree to which various points or regions in an image exhibit characteristics of particular interest. For example, characteristics that may be of interest in a breast include blob-like regions or spiculated regions, both of which could indicate malignancy. Thus, according to an embodiment, the detector 124 can include a calcification detector, blob detector, a spiculation detector, or combinations thereof. As illustrated in FIG. 1, the three-dimensional ROI detector 124 produces an ROI response image 126 that contains this characterization information for every image slice in the three-dimensional image 112.

The two-dimensional ROI extractor 128 extracts two-dimensional information from portions of the three-dimensional image 112 that include the points or regions of interest exhibiting the characteristics of interest. According to an embodiment, the extractor 128 extracts a 2D binary mask 130, also referred to herein as a chip 130, for each ROI.

According to an embodiment, the image blending unit 132 includes a blending function or process that combines the two-dimensional information extracted by the extractor 128 with the two-dimensional image 118 provided by source 116. The blending function/process forms the ROI-enhanced two-dimensional image 140.

Figure 2:
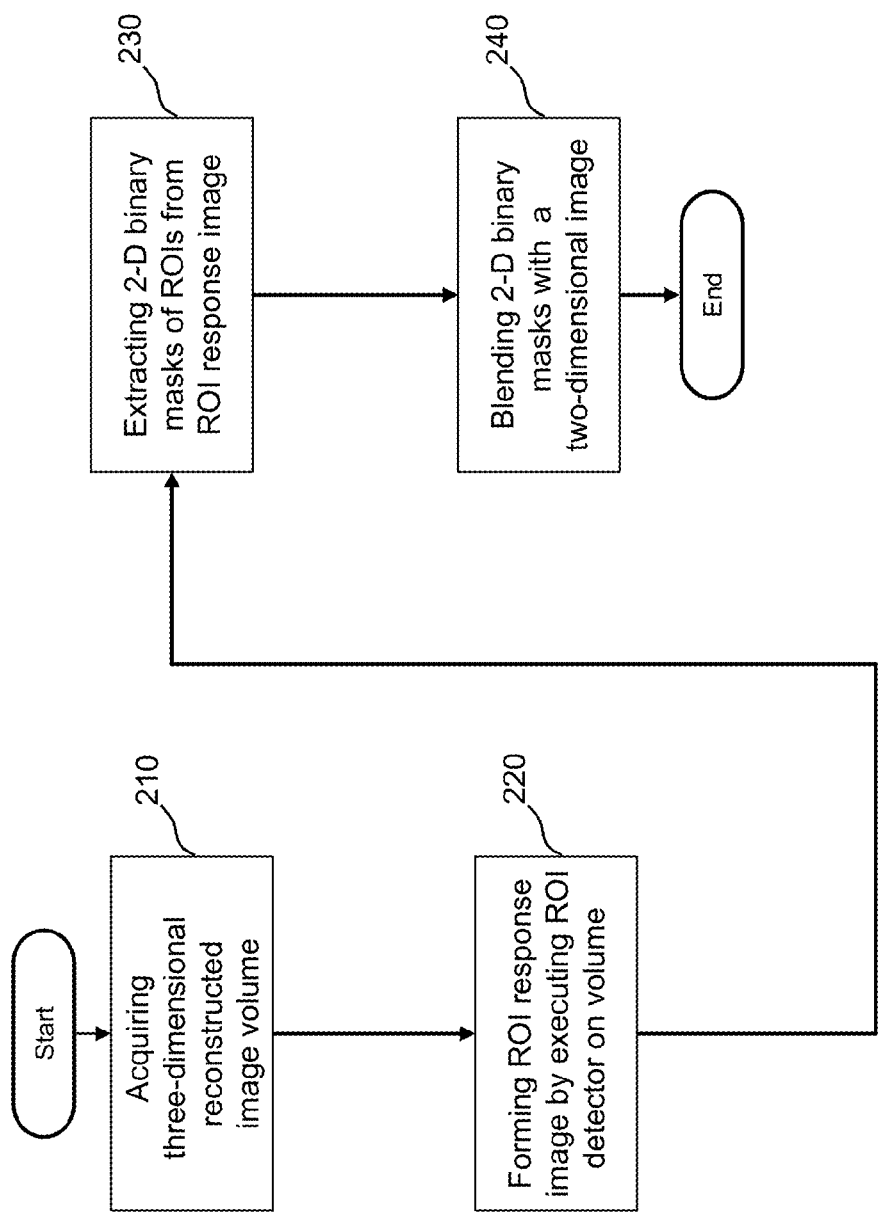
FIG. 2 is a flow diagram of an illustrative image processing process that can be performed by the medical imaging system of FIG. 1.

FIG. 2 is a flow diagram of the operational image processing that can be performed by the medical imaging system 100 to produce an ROI-enhanced two-dimensional image.

At a step 210, a three-dimensional, reconstructed image volume of an anatomical region is acquired from the three-dimensional image source 110.

At a step 220, the three-dimensional ROI detector 124 processes the 3D reconstructed image volume of the anatomical region to form the ROI response image 126.

At a step 230, the ROI extractor 128 extracts 2D binary masks of ROIs from the ROI response image 126. According to an embodiment, the ROI extractor 128 first finds the local maxima of ROIs in the response image. A local maximum specifies the 2D slice of the three-dimensional image from which the binary mask should be optimally extracted. Then, the ROI extractor 128 extracts the 2D binary mask of the ROI by thresholding the response image. In one embodiment, the threshold value to be applied is a fixed variable whose value can be set using empirical data. Finally, the ROI extractor 128 performs a mathematical morphological dilation operation to ensure that the extracted 2D binary mask will encompass the entire structure of interest.

At a step 240, the image blending unit 132 blends each 2D binary mask into the two-dimensional image 118. According to an embodiment, the blending unit 132 first computes a soft blending mask from the 2D binary mask, which will ensure that the ROIs are smoothly blended into the final image. An illustrative technique for computing the soft blending mask involves applying a known Gaussian smoothing filter on the 2D binary mask. Then, the blending unit 132 performs the following blending function:

For each pixel i in the mixed_image $$\text{mixed\_image}[i] = \text{original\_image}[i] * (1 - \text{soft\_mask\_value}[i]) + \text{chip\_image}[i] * \text{soft\_mask\_value}[i]$$

In this function, original_image[i] refers to the pixel intensity of the two-dimensional image 118, the soft_mask_value[i] refers to the pixel intensity in the soft blending mask, and the chip_image[i] refers to the pixel intensity in the 2D binary mask.

Figure 3:
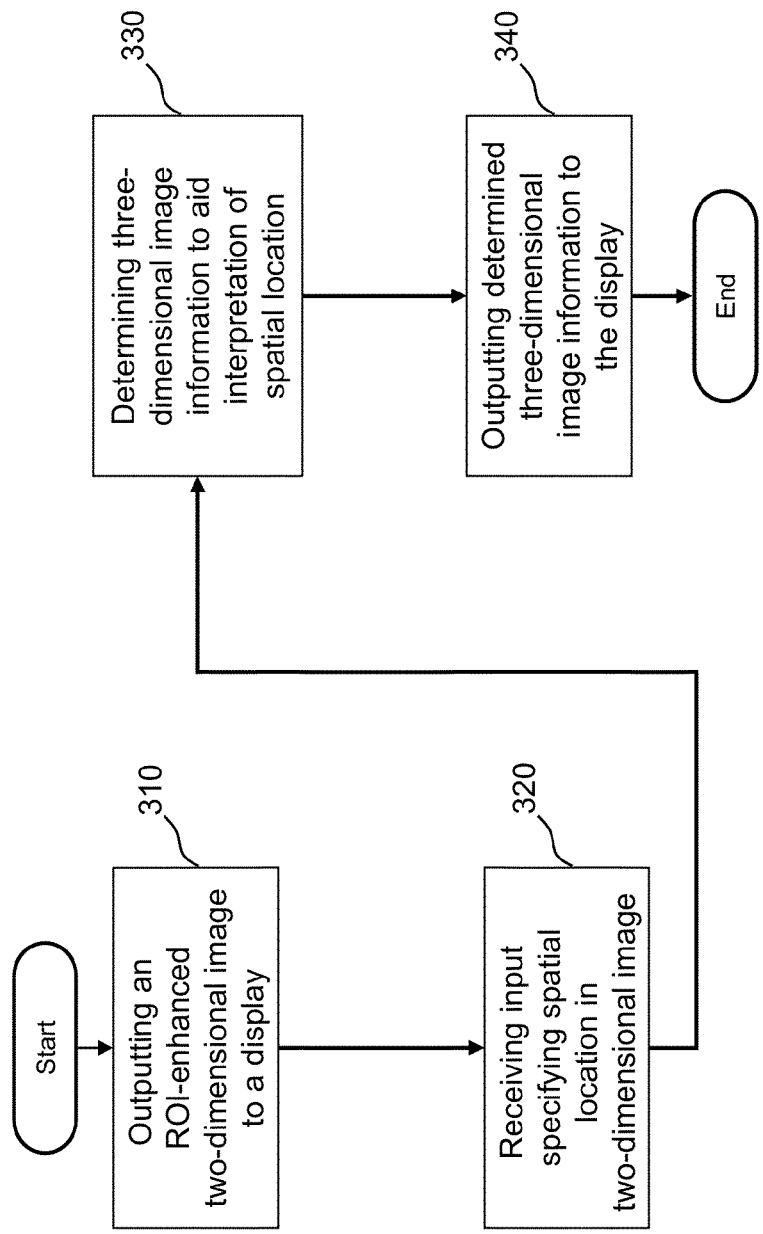
FIG. 3 is a flow diagram of an illustrative process for using a region of interest (ROI) enhanced two-dimensional image to improve the efficiency with which a viewer/diagnostician (physician, radiologist, etc.) reads medical image datasets.

FIG. 3 is a flow diagram of an illustrative process in which system 100 uses a region of interest (ROI)-enhanced two-dimensional image to improve the efficiency with which a physician reads medical image datasets.

At a step 310, the system 100 outputs an ROI-enhanced 2D image to a display, such as the graphic user interface 142 described with reference to FIG. 1.

At a step 320, the system 100 receives input specifying a spatial x, y coordinate location in the 2D image. For example, the input can specify a point or region in the 2D image that is of further interest to the physician/diagnostician.

At a step 330, the system 100 programmatically determines three-dimensional image information that would optimally aid the physician's task of interpreting the specific point or region of interest. According to an embodiment, the system 100 utilizes a three-dimensional response image to make this determination. As previously described, a three-dimensional response image characterizes the degree to which various points or regions in an image exhibit characteristics of particular interest. The system 100 identifies the slice of the three-dimensional response image where the specified spatial point exhibits the local maxima (i.e., the point or region of interest is most blob-like, most spiculated, etc.)

At a step 340, the system 100 outputs the three-dimensional image information that includes the spatial point exhibiting the local maxima to a display. By way of one example, the system 100 outputs the specific slice identified in the previous step. By way of another example, the system 100 computes a slab image that includes the spatial point and outputs the slab image to the display.

To again summarize, the illustrative system and method effectively increases the efficiency of a physician/diagnostician (e.g. radiologist) in reading tomography images. Typically, reviewing the 3D data is time-consuming and labor-intensive for such personnel. Specifically, in this modality, masses are visible and sharpest in only one or two slices of the 3D reconstructed data, which can be part of a large volume of slices. Thus, the viewer often must review all slices or slabs in the data set. When the data is projected onto a 2D projection using traditional methods, structures that exist above or below the object (mass) tends to obstruct the view, possibly occluding the mass, posing a significant challenge in identifying such an object in the 2D projection image. However, if the system can effectively identify the region of the mass before generating the 2D projection image, then the projection process can be modified to ignore confusing structures above and below the mass to produce a much clearer view in the 2D projection. The end result is a 2D projection in which the masses are also clearly visible, and generally free of any obstructions that could occlude a clear view of the object (mass) of interest. Advantageously, it is contemplated that this illustrative process can also be adapted and applied to spiculated masses and calcifications in a manner clear to those of skill.

Illustratively, the process can operate to first identifies the object of interest in the 3D data, determines the best slice(s) that reveal this object, segments and extracts the region, and then smoothly merges the result with the traditional 2D projection.

Figure 4:
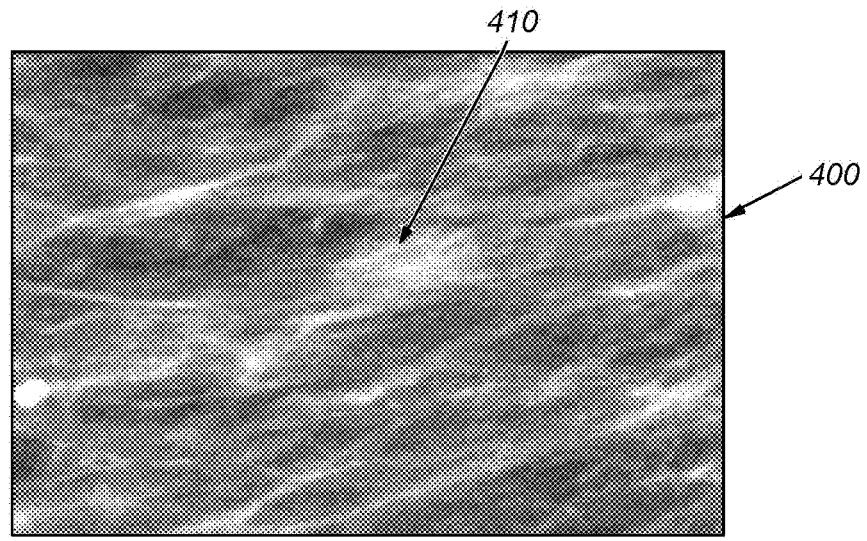
FIG. 4 is a display image of an exemplary 2D projection containing an object of interest without processing according to the illustrative embodiment.
Figure 5:
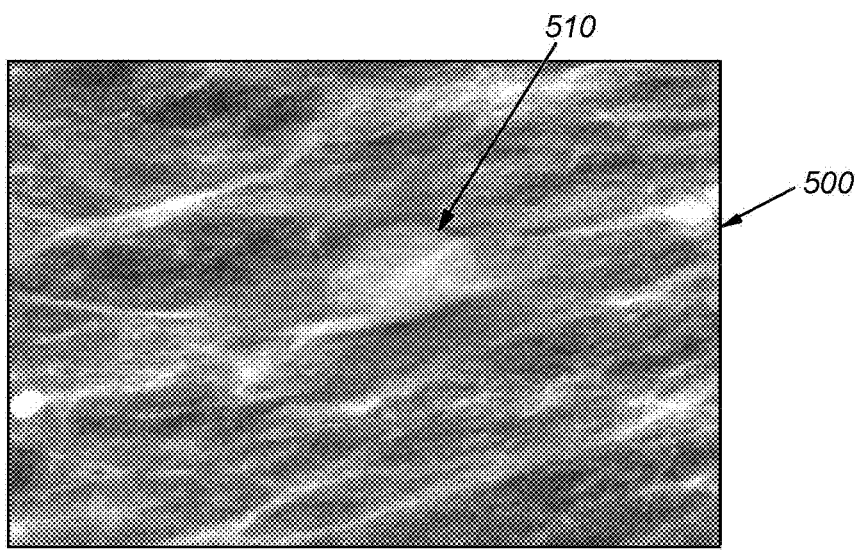
FIG. 5 is a display image of an exemplary 2D projection containing the object of interest of FIG. 4 after enhancement processing according to the illustrative embodiment.

The difference between a 2D-projected image before and after processing according to the illustrative system and method is shown in the respective exemplary display images 400 and 500 of FIGS. 4 and 5. These images are close-up views of a region of interest containing an object of interest (a suspected tumor and/or mass) in the center of the image. As shown in the display image 400 of FIG. 4 the object of interest 410 is fuzzy and contains poorly defined (not sharp) boundaries, rendering it sometimes challenging to identify without close study of the images. Conversely, the exemplary display image 500 of FIG. 5, which is a projected 2D image that has undergone the process of the illustrative system and method, displays the object of interest 510 with more-defined, sharp boundaries. This renders the object 510 more-readily identified by a viewer, thereby increasing diagnostic accuracy, efficiency and throughput.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, additional image handling algorithms/processes can be included in the overall system process to enhance or filter image information accordingly. Accordingly, this description is meant to be taken only by way of example, and not to otherwise limit the scope of this invention.

What is claimed is:

1. A system for processing image data relative to an imaged anatomical region comprising:
   a. a detection and extraction process that detects and extracts one or more two-dimensional (2D) regions of interest (ROIs) containing an object of interest from a three-dimensional (3D) medical image of the anatomical region;
   b. a first 2D projection image of the anatomical region obtained from a medical image source;
   c. a blending process that generates a second 2D projection image of the anatomical region by blending the one or more 2D ROIs onto the first 2D projection image to generate the second 2D projection image of the anatomical region; and
   d. at least one of a display and a data storage arrangement receiving an output of the second 2D projection image.

2. The system as set forth in claim 1 wherein the detection and extraction process includes an ROI detector that forms at least one ROI response image.

3. The system as set forth in claim 2 wherein the detection and extraction process is constructed and arranged to extract 2D binary masks of the one or more ROIs from at least one ROI response image.

4. The system as set forth in claim 3 wherein the detection and extraction process is constructed and arranged to blend the 2D binary masks with the first 2D projection image to generate the second 2D projection image.

5. The system as set forth in claim 1 further comprising a three-dimensional response image based upon a selected portion of the second 2D projection image that characterizes the degree to which various points or regions in an image exhibit characteristics interest.

6. A method for processing image data relative to an imaged anatomical region comprising the steps of:
   a. detecting and extracting one or more two-dimensional (2D) regions of interest (ROIs) containing an object of interest from a three-dimensional (3D) medical image of the anatomical region;
   b. defining a first 2D projection image of the anatomical region obtained from a medical image source;
   c. generating a second 2D projection image of the anatomical region by blending the one or more 2D ROIs onto the first 2D projection image to generate the second 2D projection image of the anatomical region; and
   d. at least one of (i) displaying and (ii) storing an output of the second 2D projection image.

7. The system of claim 1 wherein the one or more 2D ROIs are each being constructed from the 3D medical image as a thin image slice.

8. The system of claim 7 wherein each thin image slice has a spatial resolution of 100 microns per pixel.

9. The system of claim 7 wherein each thin image slice has a thickness of approximately 1 millimeter.

10. The system of claim 7 wherein each thin image slice has dimensions of at least 2500 rows of pixels by at least 1500 columns of pixels.

11. The system of claim 1 wherein the blending process performs the blending on each pixel based upon a pixel intensity in the 2D image.

12. The method of claim 6 wherein the detecting and extracting further comprises forming at least one response image using an ROI detector.

13. The method of claim 12 wherein the detecting and extracting further comprises extracting 2D binary masks of the one or more ROIs from at least one ROI response image.

14. The method of claim 13 wherein the detecting and extracting further comprises blending the 2D binary masks with the first 2D projection image to generate the second 2D projection image.

15. A system for processing image data relative to an imaged anatomical region, the system comprising:
    means for detecting and extracting one or more two-dimensional (2D) regions of interest (ROIs) containing an object of interest from a three-dimensional (3D) medical image of the anatomical region;
    means for defining a first 2D projection image of the anatomical region obtained from a medical image source;
    means for generating a second 2D projection image of the anatomical region by blending the one or more 2D ROIs onto the first 2D projection image to generate the second 2D projection image of the anatomical region; and
    means for at least one of (i) displaying and (ii) storing an output of the second 2D projection image.

16. The system of claim 15 wherein the means for detecting and extracting comprises a detecting and extracting process.

17. The system of claim 15 wherein the means for generating a second 2D projection image comprises a blending process.

18. The system of claim 15 further comprising a reconstruction processing unit that constructs the image volume in 40-60 thin image slices for analysis by the detection and extraction process.

19. The system of claim 1, wherein the medical image source comprises a computer memory.

20. The system of claim 1, wherein the medical image source comprises a tomosynthesis image acquisition unit.

21. The method of claim 6, wherein the medical image source comprises a computer memory.

22. The method of claim 6, wherein the medical image source comprises a tomosynthesis image acquisition unit.

23. The system of claim 15, wherein the medical image source comprises a computer memory.

24. The system of claim 15, wherein the medical image source comprises a tomosynthesis image acquisition unit.

* * * * *